(12) United States Patent
Renzi et al.

(10) Patent No.: US 6,812,265 B1
(45) Date of Patent: Nov. 2, 2004

(54) LIQUID COMPOSITION POLYMERIZABLE INTO ORGANIC GLASSES HAVING GOOD OPTICAL AND PHYSICO-MECHANICAL PROPERTIES

(75) Inventors: Fiorenzo Renzi, Cervia (IT); Andrea Bendandi, Ravenna (IT); Roberto Forestieri, Ravenna (IT); Nereo Nodari, Ravenna (IT)

(73) Assignee: Great Lakes Chemical (Europe) GmbH (CH)

( * ) Notice: Subject to any disclaimer, the term of this patent is extended or adjusted under 35 U.S.C. 154(b) by 0 days.

(21) Appl. No.: 09/830,841

(22) PCT Filed: Nov. 5, 1999

(86) PCT No.: PCT/EP99/08388

§ 371 (c)(1),
(2), (4) Date: May 1, 2001

(87) PCT Pub. No.: WO00/27794

PCT Pub. Date: May 18, 2000

(30) Foreign Application Priority Data

Nov. 6, 1998 (IT) .......................................... MI98A2411

(51) Int. Cl.⁷ ............................. C08F 2/46; C08G 63/66

(52) U.S. Cl. ............................. 522/24; 522/35; 528/275; 528/288; 528/300; 528/301; 528/370; 528/371; 528/392; 524/81; 524/777

(58) Field of Search .................................. 528/275, 288, 528/300, 301, 370, 371, 392; 524/81, 777; 522/24, 35

(56) References Cited

U.S. PATENT DOCUMENTS 4,970,293 A    11/1990  Renzi et al. ................. 528/370

*Primary Examiner*—Samuel A. Acquah
(74) *Attorney, Agent, or Firm*—Michael W. Ferrell

(57) ABSTRACT

Liquid composition which can be polymerized into organic glasses, by means of radical polymerization with low shrinkage, comprising the product obtained from the trans-esterification of a diallycarbonate (A) with a mixture of one or more linear or branched aliphatic diols (B), containing from three to ten carbon atoms in the molecule, with a linear or branched aliphatic polyol (C), containing from four to twenty carbon atoms and from three to six hydroxyl groups in the molecule. The molar ratio A/(B+C) in the above polymerizable liquid composition ranges from 2/1 to 5/1 and the quantity of (C) in the mixture (B+C) is equal to or less than 25% by weight with respect to the total weight of this mixture.

27 Claims, No Drawings

LIQUID COMPOSITION POLYMERIZABLE INTO ORGANIC GLASSES HAVING GOOD OPTICAL AND PHYSICO-MECHANICAL PROPERTIES

The present invention relates to a liquid composition polymerizable into organic glasses.

More specifically, the present invention relates to a liquid composition which can be polymerized, by means of radical polymerization with low shrinkage, into organic glasses having good optical and physico-mechanical properties, comprising the product obtained from the transesterification of a diallyl carbonate (A) with a mixture of one or more diols (3) with a polyol (C).

A further object of the present invention relates to the organic glasses obtained from the polymerization of said composition.

Finally, the present invention also relates to the end-articles obtained starting from said composition, such as for example, ophthalmic lenses and solar filters, protective shields, sight windows, solar and photovoltaic collectors and panels, substrates for optical disks, panels for display and video terminals.

In the field of high transparency organic glasses, the product obtained from the polymerization of diethylene glycol bis(allyl carbonate) is of great commercial interest in the production of ophthalmic and safety plates and lenses, owing to its special mechanical and age-resistance characteristics, as described, for example, by F. Strain, in: "Encyclopedia of Chemical Processing and Design", First Edition, Dekker Inc., New York, Vol. 11, page 452 onwards; and in "Encyclopedia of Polymer Science and Technology" (196.4), Vol. 1, page 799 onwards, Interscience Publishers, New York.

The use of diethylene glycol bis(allyl carbonate), however, has various disadvantages which limit and, at times, prevent its use in different fields of application.

For example, the shrinkage which accompanies the polymerization reaction of bis (allyl carbonate) in the presence of peroxide initiators, makes the preparation of high power lenses difficult. The abrasion resistance of the organic glasses thus obtained, although much higher than that of other known organic glasses, still cannot be considered as being optimum: this is demonstrated by the fact that it is customary to resort to the surface application of scratch-proof coatings on this organic glass.

Not even the impact strength of the above organic glasses, although its value is sufficient to pass the tests imposed by the regulations in force in the optical field, can be considered as being optimum.

Numerous compositions polymerizable into organic glasses have been described in an effort to overcome these drawbacks and to improve some of the most important characteristics of organic glasses.

For example, the patent U.S. Pat. No. 4,812,545, discloses liquid compositions polymerizable into organic glasses comprising tris(hydroxyethyl)isocyanurate tris(allyl carbonate); and diethylene glycol bis(allyl carbonate) monomeric and oligomeric, having an improved shrinkage during polymerization and a better impact strength.

The patent U.S. Pat. No. 4,713,433 on the other hand, describes liquid compositions polymerizable into organic glasses comprising oligomeric bis(allyl carbonate) and a comonomer having at least four terminal allyl groups capable of producing organic glasses with an improved abrasion resistance.

Finally, the patent U.S. Pat. No. 4,970,293 discloses liquid compositions polymerizable into organic glasses comprising the reaction product of a diallyl carbonate with mixtures of a diol and a polyol containing from three to six hydroxyl groups per molecule. However, although these compositions on the one hand effectively represent an improvement in some specific characteristics of the organic glasses obtained from their polymerization, on the other hand, !they have other characteristics which are worse than those of the organic glasses obtained from the polymerization of diethylene glycol bis(allyl carbonate) alone.

As already mentioned above, the organic glass obtained from the polymerization of diethylene glycol bis(allyl carbonate) alone has various disadvantages: for example, it often has yellow index values higher than those normally acceptable, and/or unacceptable refraction index values, and/or impact strenght values, and/or dyeability values. As a result, diethylene glycol bis(allyl carbonate) cannot be used alone but, as specified above, must be mixed with other comonomers which, however, have other drawbacks.

In this respect, it should be remembered that the organic glass obtained as described in the patent U.S. Pat. No. 4,970,293 mentioned above, is particularly useful in protective shields (for example, for welders), in sight windows (for example, in blast furnaces), in windows in the transport and civil industry, in lenses for vehicle lights, in solar and photovoltaic collectors and panels, in substrates for optical disks and in panels for display, but it cannot be used for optical lenses as it has a high yellow index, a low impact strenght, a poor dyeability.

The Applicant has now found a liquid composition which can be, easily polymerized by means of radical polymerization with low shrinkage, into organic glasses having good optical and physico-mechanical properties, capable of overcoming the drawbacks of the known art described above.

The present invention therefore relates to a liquid composition which can be polymerized by means of radical polymerization with low shrinkage, into organic glasses, comprising the product obtained from the transesterification of a diallyl carbonate (A) with a mixture of one or more linear or branched aliphatic diols (B), containing from three to ten carbon atoms in the molecule with a linear or branched aliphatic polyol (C), containing from four to twenty carbon atoms and from three to six hydroxyl groups in the molecule, wherein the molar ratio (A)/(B+C) ranges from 2.5/1 to 4/1, and the quantity of (C) in the mixture (B+C) ranges from 5% by weight to 20% by weight with respect to the total weight of the mixture (B+C).

Diols (B) which can be used for the purposes of the present invention, as already mentioned above, are linear or branched aliphatic diols, containing from three to ten carbon-atoms in the molecule.

Specific examples of diols (B) which can be used for the purposes of the present invention are: diethylene glycol, triethylene glycol, tetraethylene glycol, 1,4-butanediol, 1,6-hexanediol, 1,3-propanediol, neopentylglycol, dipropyleneglycol, 2,2,4-trimethyl-1,3-pentanediol, etc.

Preferred diols for the purposes of the present invention are diethylene glycol and neopentylglycol.

Polyols (C) which can be used for the purposes of the present invention, as already mentioned above, are linear or branched aliphatic polyols, containing from four to twenty carbon atoms and from three to six hydroxyl groups in the molecule.

Specific examples of polyols (C) which can be used for the purposes of the present invention are: pentaerythritol, trimethylolpropane, dipentaerythritol, ditrimethylolpropane, tris(hydroxyethyl)isocyanurate, etc.

Preferred polyols for the purposes of the present invention are pentaerythritol and trimethylolpropane.

The polymerizable liquid composition of the present invention is obtained starting from diallyl carbonate (A) and the mixture (B+C) operating under transesterification conditions. More specifically, the reagents are put in contact with each other, in the ratios indicated above, and reacted at a temperature ranging from 80° C. to 160° C., preferably from 90° C. to 130° C., in the presence of a catalyst of the alkaline type, continuously eliminating the allyl alcohol formed as reaction by-product.

Catalysts of the alkaline type which can be used for the purposes of the present invention are: hydroxides, carbonates and alcoholates of alkaline metals, organic bases, basic ion-exchange resins.

Specific examples of catalysts of the alkaline type used for the purposes of the present invention are: sodium hydroxide, sodium carbonate, sodium methylate.

The catalyst is conveniently used in a quantity equal to at least 1 ppm (parts per million by weight) with respect to the sum of the weights of components (B+C) and, preferably, in a quantity ranging from 0.01% to 0.3% by weight.

The above transesterification reaction is conveniently carried out at such a pressure as to bring the system to boiling point at the preselected operating temperature, in order to favour the elimination, of the allyl alcohol from the reaction mixture: for example, pressure values ranging from 60 mbar to 1030 mbar, preferably from 60 mbar to 500 mbar, are suitable for the purpose.

Operating under the conditions described above, the reaction times generally range from 0.5 hours to 20 hours, preferably from 0.5 hours to 3 hours.

After cooling, the above reaction mixture is washed with water to remove the small quantities of residual catalyst and, after separation and removal of the aqueous phase, the non-reacted diallyl carbonate is eliminated by distillation, heating to a temperature in the order of 130° C., under decreasing pressure with end-values ranging from 0.1 mbar to 20 mbar, preferably from 0.5 mbar to 2 mbar, obtaining the desired composition, as residue.

The composition thus obtained is finally subjected to filtration after optional treatment with activated carbon.

The composition of the present invention is liquid at room temperature and has viscosity values ranging from 15 cts to 300 cts and density values ranging from 1.1 g/ml to 1.3 g/ml.

The polymerizable liquid composition of the present invention is a complex mixture which contains allyl carbonates of component (B) and component (C), in monomeric and oligomeric form, as well as mixed oligomeric allyl carbonates of these compounds (B) and (C), the relative quantities of these constituents of the present composition mainly depending on the pre-established ratios of reagents (A), (B) and (C).

The above composition can be transformed into organic glasses, by means of radical polymerization, using the usual "casting" technique.

For this purpose, one or more polymerization initiators are added to the composition, which are soluble in the composition itself and capable of generating free radicals within a temperature range of 30° C. to 120° C.

A group of polymerization initiators which can be used for the purposes of the present invention is the group of peroxides.

Preferred examples of peroxides which can be used for the present invention are: dicyclohexylperoxydicarbonate, diisopropylperoxydicarbonate, dibenzoylperoxide, di-s-butyl-peroxydicarbonate, s-butylcyclohexylperoxydicarbonate, etc.

Other peroxides which can be used for the purposes of the present invention are perketals.

Preferred examples of perketals which can be used in the present invention are: 1,1-di-(t-butylperoxy)-cyclohexane, 1,1-di-(t-butylperoxy)-3,3,5-trimethyl-cyclohexane, 1,1-di-(t-amylperoxy)-cyclohexane, 1,1-di-(t-butylperoxy)-2-methylcyclohexane, 1,1-di-(t-amylperoxy)-2-methylcyclohexane, etc.

The quantity of initiator used may generally vary within a range of 1 to 6 parts by weight for every 100 parts by weight of the composition of the present invention.

The composition of the present invention may optionally contain one or more conventional additives such as, for example, oxidization, light and heat stabilizers, lubricants, dyes, pigments, UV-absorbers, IR-absorbers, and the like, in a total quantity however not exceeding 1 part by weight for every 100 parts by weight of the compositions themselves.

Examples of additives which can be used for the purposes of the present invention are: sterically hindered phenols, sterically hindered amines, benzophenones, benzotriazoles, organic phosphites and phosphonites, etc.

The composition of the present invention containing the polymerization initiator and, optionally, one or more additives selected from those mentioned above, is transformed into the relative organic glasses, operating at temperatures ranging from 30° C. to 120° C., with polymerization times which can generally vary from 1 hour to 100 hours.

During the polymerization there is a limited shrinkage and the organic glasses thus obtained have good optical and physico-mechanical properties.

These organic glasses are particularly useful in the production of ophthalmic lenses and solar filters, protective shields, sight windows, solar and photovoltaic collectors and panels, substrates for optical disks, panels for display and video terminals: these end-articles are therefore a further object of the present invention.

Some illustrative examples are provided for a better understanding of the present invention and for its embodiment, but should not be considered as limiting the scope of the invention in any way.

In the following examples polymerizable liquid compositions are prepared by reacting, under transesterification conditions, the diallyl carbonate (A) and a mixture of compounds (B) and (C).

The diol (B) used in the examples is diethylene glycol (DIG).

The polyol (C) used in the examples is pentaerythritol (PE)

Dicyclohexylperoxydicarbonate (CHPC) is added to the liquid compositions thus obtained, as polymerization initiator, in a quantity equal to 5% by weight with respect to the weight of the composition.

The compositions containing the polymerization initiator are transformed, by means of polymerization, into flat sheets or neutral lenses, using the "casting" technique. Operating according to this technique, the liquid compositions, containing the polymerization initiator, are poured into the cavity of a mould consisting of two glass elements and having a spacer gasket of plasticized polyvinylchloride, of ethylene-vinylacetate (EVA) copolymer, of low density polyethylene (LDPE), or of any other suitable material, compatible with the operating conditions.

The liquid compositions are then subjected to polymerization by means of thermal treatment in a forced circulation oven, with a gradual temperature rise from 35° C. to 80° C. in twenty hours.

At the end of the above treatment, the moulds are opened and the polymerized products are recovered and maintained at 110° C. for an hour to complete the polymerization reaction and give the end-article dimensional stability.

The following characteristics are determined on the sheets thus obtained:

(a) Optical Characteristics

Refractive index ($n_D^{20}$): measured with an Abbe refractometer (ASTM D-542).

Yellow index (YI) (ASTM D-1925) defined as $$YI = \frac{100}{Y}(1.277X - 1.06Z)$$

determined with a Macbeth 1500 Plus spectrophotometer.

(b) Physical and Mechanical Characteristics

Density: determined with hydrostatic balance at a temperature of 20° C. (ASTM D-792).

Shrinkage during polymerization calculated with the following formula:

$$\% \text{ shrinkage} = \frac{(\text{polymer density} - \text{monomer density})}{(\text{polymer density})} \times 100$$

Rockwell Hardness (M) measured with a Rockwell durometer (ASTM D-785).

Izod impact strenght without notch (ASTM D-256 modified)

(c) Thermal Characteristics

Deflection temperature under load 1.82 Mpa (HDT) (ASTM D-648).

(d) Abrasion Resistance

To evaluate the abrasion resistance the Sutherland rub tester is used. The test consists in carrying out 50 passages with a 2/0 type steel wool bearing loaded with a weight of 2 kg on a neutral sample lens.

The abrasion degree produced is evaluated by measuring the Haze % increase (% of diffused light transmitted with respect to the total light transmitted) following scratches produced on the surface of the lens.

The Haze values are determined before and after the abrasion test using a Hazegard XL-211 device of Gardner, in accordance with the regulation ASTM D-1003.

A higher Haze value obviously indicates a greater degree of diffused light transmitted and consequently a lower abrasion resistance (more scratched lens).

(e) Dyeability

The capacity to adsorb a dye on the surface of the material is determined by the immersion of a neutral lens in an aqueous bath in which the dye BPI Guy is dispersed.

For this purpose the lens is immersed in this colouring bath for 30 minutes at a temperature of 80° C. and, after rinsing with demineralized water, the light transmittance of the lens is determined by measuring the Y chromatic coordinate as described by CIE (1931) Standard Observer.

It can be clearly seen from the following examples that the compositions of the present invention, as well as having a reduced shrinkage during polymerization, allow the production of organic glasses having improved characteristics with respect to the organic glasses of the known art:

refractive index equal to that of the organic glasses obtained from the polymerization of diethylene glycol bis(allyl carbonate) alone (this allows the use of the same glass moulds with a consequent reduction in the investment costs);

reduced yellow index;

high impact strenght;

high abrasion resistance;

good dyeability.

EXAMPLE 1

The following products are charged into a three-necked, jacketed flask, equipped with a thermometer and magnetic stirrer and overhead with a distillation column with 10 perforated trays having a diameter of 30 mm:

pentaerythritol (PE): 34.5 g (0.25 moles);

diethylene glycol (DEG): 223 g (2.10 moles);

diallyl carbonate (DAC): 1000 g (7.04 moles);

solution at 20% by weight of sodium methylate in methanol (1.20 ml).

The reaction is carried out for 3 hours at a temperature of 83° C.–120° C. and at a pressure decreasing from 190 mbar to 130 mbar, and distilling the allyl alcohol as it is formed (total 346 ml; purity>99.0%).

After cooling, the reaction mixture is washed with two portions, each of 500 ml, of distilled water.

The excess of diallyl carbonate is distilled at a pressure of about 1 mbar, operating at a temperature increasing up to 130° C.: the product obtained is filtered with a 0.45 μm membrane.

525 g of a liquid product are thus obtained, having the following characteristics:

viscosity (25° C.): 75 cst;

density (20° C.): 1.1.92 g/ml;

refractive index ($n_D^{20}$): 1.461;

APHA colour: 5

The above product is a mixture of diethylene glycol bis(allyl carbonate) monomer and oligomers, of pentaerythritol tetrakis(allyl carbonate) monomer and oligomers, and mixed allyl carbonates, having the following composition determined by liquid column chromatography (HPLC; ELDS detector):

80% by weight of diethylene glycol bis(allyl carbonate) monomer (n=1) and oligomers (n>1), having the formula:

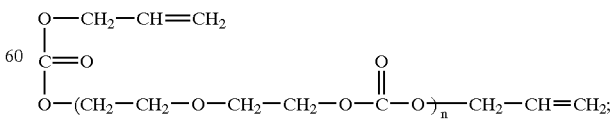

3% by weight of pentaerythritol tetrakis(allyl carbonate), monomer (n=1) and oligomers (n>1), having the formula:

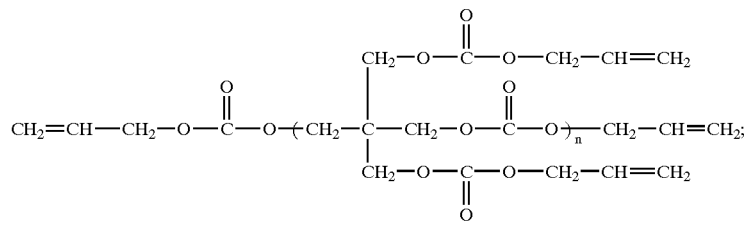

12% by weight of mixed allyl carbonate having the formula:

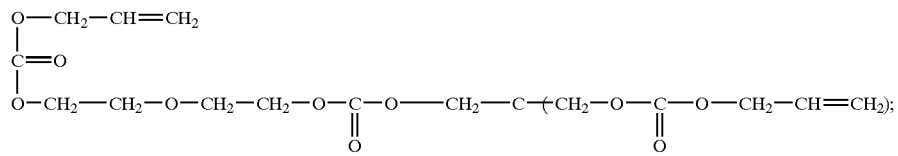

the remaining percentage essentially consisting of higher oligomers of the previous species.

The above composition, after the addition of dicyclohexylperoxydicarbonate (CHPC; 5 by weight in the composition), is subjected to polymerization operating as described above, and the characteristics indicated in Table 1 are determined on the hardened composition.

Table 1 indicates, for comparative purposes, the properties of the composition obtained from the polymerization of diethylene glycol bis(allyl carbonate) alone and the composition obtained from the polymerization of the liquid composition described in Example 3 of the patent U.S. Pat. No. 4,970,293: the polymerization conditions are obviously the same as those used for the composition object of the present invention above described.

The yellow index (YI) is determined on a sample having a thickness of 5 mm to which 2-hydroxy-4-methoxybenzophenone has been added (0.1%).

TABLE 1

|  | Composition Example 1 | Diethylene glycol bis(allyl carbonate) | Composition Example 3 of U.S. Pat. No. 4,970,293 |
|---|---|---|---|
| Density (20° C.) | 1.328 | 1.311 | 1.333 |
| Shrinkage (%) | 10.2 | 12.1 | 10.5 |
| Refractive index ($n_D^{20}$) | 1.500 | 1.500 | 1.502 |
| Yellow index (YI) | 1.6 | 1.7 | 2.9 |
| Rockwell Hardness (M) | 100 | 98 | 116 |
| Izod impact strength without notch (KJ/m$^2$) | 30 | 25 | 14 |
| HDT (° C.) | 61 | 62 | 143 |
| Sutherland abrasion resistance (Haze %) | 0.4 | 1.0 | 0.2 |
| Dyeability (Y) | 42.9 | 38.3 | 76.2 |

EXAMPLE 2

Operating as described in Example 1, the following compositions 2, 3 and 4 are prepared, by reacting diallyl carbonate (DAC) with mixtures of pentaerythritol (PE) and diethylene glycol (DEG), in various molar ratios (DAC/(PE+DEG), as indicated in Table 2.

Table 2 also indicates the viscosity (cst; 25° C.), density (g/ml; 20° C.), and refraction index ($n_D^{20}$) characteristics of the polymerizable liquid compositions obtained.

TABLE 2

| Composition Nr. | | 2 | 3 | 4 |
|---|---|---|---|---|
| Mixture | PE (weight %) | 11.6 | 12 | 11 |
|  | DEG (weight %) | 88.4 | 88 | 89 |
| DAC/(PE + DEG) | | 2.7/1 | 3.2/1 | 3.4/1 |
| Viscosity (cst; 25° C.) | | 92.3 | 61 | 56 |
| Density (g/ml; 20° C.) | | 1.194 | 1.190 | 1.187 |
| $N_D^{20}$ | | 1.461 | 1.460 | 1.459 |

The above compositions, after the addition of dicyclohexylperoxydicarbonate (CHPC; 5% by weight in the composition), are subjected to polymerization operating as described above and the characteristics indicated in Table 3 are determined on the hardened compositions.

Also in this case, the yellow index (YI) is determined on a sample having a thickness of 5 mm and to which 2-hydroxy-4-methoxybenzophenone has been added (0.1%).

TABLE 3

|  | Composition Nr. 2 | Composition Nr. 3 | Composition Nr. 4 |
|---|---|---|---|
| Density (20° C.) | 1.326 | 1.325 | 1.350 |
| Shrinkage (%) | 9.9 | 10.2 | 10.4 |
| Refractive index ($n_D^{20}$) | 1.499 | 1.500 | 1.500 |
| Yellow index (YI) | 1.6 | 1.6 | 1.7 |
| Rockwell Hardness (M) | 95 | 95 | 100 |
| Izod impact strength without notch (KJ/m$^2$) | 39 | 34 | 42 |
| HDT (° C.) | — | 60 | 61 |
| Sutherland abrasion resistance (Haze %) | 0.4 | 0.35 | 0.45 |
| Dyeability (Y) | 39.8 | 41.8 | 40.2 |

What is claimed is:
1. A liquid composition which is polymerizable, by means of radical polymerization with low shrinkage, into organic glasses, comprising the product obtained from the transesterification of a diallylcarbonate (A) with a mixture of one or more linear or branched aliphatic diols (B), containing from three to ten carbon atoms in the molecule with a linear or branched aliphatic polyol (C), containing from four to twenty carbon atoms and from three to six hydroxyl groups in the molecule, wherein the molar ratio (A)/(B+C) ranges from 2.5/1 to 4/1 and the quantity of (C) in the mixture (B+C) ranges from 5% by weight to 13.4% by weight with respect to the total weight of said mixture (B+C).

2. The composition according to claim 1, wherein the diols (b) are: diethylene glycol, triethylene glycol, tetraethylene glycol, 1,4-butanediol, 1,6-hexanediol, 1,3-propanediol, neopentylglycol, dipropyleneglycol, 2,2,4-trimethyl-1,3-pentaendiol.

3. The composition according to claim 2, wherein the diols are diethylene glycol and neopentylglycol.

4. The composition according to claim 1, wherein the polyols (c) are:

pentaerythritol, trimethylolpropane, dipentaerythritol, ditrimethylolpropane, tris(hydroxyethyl) isocyanurate.

5. The composition according to claim 4, wherein the polyols are pentaerythritol and trimethylolpropane.

6. The composition according to claim 1, obtained starting from diallyl carbonate (A) and from the mixture (B+C) operating under transesterification conditions, at a temperature ranging from 80° C. to 160°, in the presence of a catalyst of the alkaline type, and continuously eliminating the allyl alcohol which is formed as reaction by-product.

7. The composition according to claim 6, wherein the transesterification is carried out at a temperature ranging form 90° C. to 130° C., and the catalyst of the alkaline type is selected from: hydroxides, carbonates and alcoholates of alkaline metals, organic bases, basic ion-exchange resins.

8. The composition according to claim 7, wherein the catalyst of the alkaline type is selected from: sodium hydroxide, sodium carbonate, sodium methylate.

9. The composition according to claim 6, wherein the catalyst is used in a quantity equal to at least 1 ppm (parts per million by weight) with respect to the sum of the weights of components (B+C).

10. The composition according to claim 9, wherein the catalyst is used in a quantity ranging form 0.01% to 0.3% by weight with respect to the sum of the weights of components (B+C).

11. The composition according to claim 6, wherein the transesterification reaction is carried out at pressure values ranging from 60 mbar to 1030 mbar.

12. The composition according to claim 11, wherein the transesterification reaction is carried out at pressure values ranging from 60 mbar to 500 mbar.

13. The composition according to claim 6, wherein the reaction times range from 0.5 hours to 20 hours.

14. The composition according to claim 13, wherein the reaction times range from 0.5 hours to 3 hours.

15. The composition according to claim 1, wherein one or more conventional additives are present, selected from the group consisting of oxidation, light and heat stabilizers, lubricants, dyes, pigments, UV-absorbers, and IR-absorbers, in a total quantity however not exceeding 1 part by weight for every 100 parts by weight of the compositions themselves.

16. The composition according to claim 1, wherein one or more polymerization initiators are present, which are soluble in the composition itself and generate free radicals within a temperature range of 30° C. to 120° C.

17. The composition according to claim 16, wherein the polymerization initiators belong to the group of peroxides.

18. The composition according to claim 17, wherein the peroxides are: dicyclohexylperoxydicarbonate, diisopropylperoxydicarbonate, dibenzoylperoxide, di-s-butyl-peroxydicarbonate, s-butyl-cyclohexylperoxydicarbonate.

19. The composition according to claim 16, wherein the polymerization initiators are perketals.

20. The composition according to claim 19, wherein the perketals are: 1,1-di-(t-butylperoxy)-cyclohexane, 1,1-di-(t-butylperoxy)-3,3,5-trimethyl-cyclohexane, 1,1-di-(t-amyl-peroxy)-cyclohexane, 1,1-di-(t-butyl-peroxy)-2-methyl-cyclohexane, 1,1-di-(t-amylperoxy)-2-methylcyclohexane.

21. The composition according to claim 16, wherein the quantity of initiator used varies within a range of 1 to 6 parts by weight for every 100 parts by weight of said composition.

22. The composition according to claim 16, which is transformed into the relative organic glasses operating at a temperature ranging from 30° C. to 120° C., with polymerization times which generally range from 1 hour to 100 hours.

23. Organic glasses obtained from the polymerization of the composition according to claim 1.

24. Ophthalmic lenses and solar filters, protective shields, sight windows, solar and photovoltaic collectors and panels, substrates for optical disks, panels for display, video terminals obtained from the processing of the organic glasses according to claim 23.

25. A process for manufacturing optical lenses from a liquid composition which is polymerizable, by means of radical polymerization with low shrinkage, into organic glasses, said composition comprising the product obtained from the transesterification of a diallylcarbonate (A) with a mixture of one or more linear or branched aliphatic diols (B), containing from three to ten carbon atoms in the molecule with a linear or branched aliphatic polyol (c), containing from four to twenty carbon atoms and from three to six hydroxyl groups in the molecule, wherein the molar ratio (A)/(B+C) ranges from 2.5/1 to 4/1 and the quantity of (C) in the mixture (B+C) ranges from 5% by weight to 13.4% by weight with respect to the total weight of said mixture (B+C), said process being a casting technique comprising pouring said composition containing a free radical polymerization initiator into the cavity of a mould and polymerizing the composition by means of a thermal treatment.

26. A liquid composition which is polymerizable, by means of radical polymerization with low shrinkage, into organic glasses, comprising the product obtained from the transesterification of a diallylcarbonate (A) with a mixture of one or more linear or branched aliphatic diols (B), containing from three to ten carbon atoms in the molecule with a linear or branched aliphatic polyol (C), containing from four to twenty carbon atoms and from three to six hydroxyl groups in the molecule, wherein the molar ratio (A)/(B+C) ranges from 2.5/1 to 4/1 and the quantity of (C) in the mixture (B+C) ranges from 5% by weight to a maximum of less than 20% by weight with respect to the total weight of said mixture (B+C).

27. A process for manufacturing optical lenses from a liquid composition which is polymerizable, by means of radical polymerization with low shrinkage, into organic glasses, said composition comprising the product obtained from the transesterification of a diallylcarbonate (A) with a mixture of one or more linear or branched aliphatic diols (B), containing from three to ten carbon atoms in the molecule with a linear or branched aliphatic polyol (c), containing from four to twenty carbon atoms and from three to six hydroxyl groups in the molecule, wherein the molar ratio (A)/(B+C) ranges from 2.5/1 to 4/1 and the quantity of (C) in the mixture (B+C) ranges from 5% by weight to a maximum of less than 20% by weight with respect to the total weight of said mixture (B+C), said process being a casting technique comprising pouring said composition containing a free radical polymerization initiator into the cavity of a mould and polymerizing the composition by means of a thermal treatment.

* * * * *

UNITED STATES PATENT AND TRADEMARK OFFICE
CERTIFICATE OF CORRECTION

PATENT NO. : 6,812,265 B1
DATED : November 2, 2004
INVENTOR(S) : Renzi et al.

It is certified that error appears in the above-identified patent and that said Letters Patent is hereby corrected as shown below:

Title page,
Item [*] Notice, delete "0 days" to read -- 330 days --.

Signed and Sealed this

Twenty-eighth Day of June, 2005

JON W. DUDAS
*Director of the United States Patent and Trademark Office*

UNITED STATES PATENT AND TRADEMARK OFFICE
CERTIFICATE OF CORRECTION

PATENT NO. : 6,812,265 B1 Page 1 of 1
DATED : November 2, 2004
INVENTOR(S) : Renzi et al.

It is certified that error appears in the above-identified patent and that said Letters Patent is hereby corrected as shown below:

Title page,
Item [*] Notice, change "0 days" to -- 330 days --.

Signed and Sealed this

Thirtieth Day of August, 2005

JON W. DUDAS
*Director of the United States Patent and Trademark Office*